United States Patent [19]

Kondo et al.

[11] Patent Number: 5,060,651
[45] Date of Patent: Oct. 29, 1991

[54] ULTRASONIC DIAGNOSTIC APPARATUS

[75] Inventors: Toshio Kondo, Kunitachi; Yutaka Sato, Kashiwa; Hiroshi Masuzawa, Kokubunji; Hiroshi Takeuchi, Matsudo, all of Japan

[73] Assignee: Hitachi Medical Corporation, Tokyo, Japan

[21] Appl. No.: 588,714

[22] Filed: Sep. 27, 1990

[30] Foreign Application Priority Data

Oct. 2, 1989 [JP] Japan .................................. 1-255135

[51] Int. Cl.⁵ .............................................. A61B 8/00
[52] U.S. Cl. .................. 128/660.07; 73/625; 73/626; 73/628; 128/661.01
[58] Field of Search ...................... 128/660.07, 661.01; 73/623, 625, 626, 628

[56] References Cited

U.S. PATENT DOCUMENTS

| 4,168,628 | 9/1979 | Vilkomerson | 128/661.01 |
| 4,662,222 | 5/1987 | Johnson | 128/660.07 |
| 4,674,516 | 6/1987 | Hirota et al. | 128/661.01 |
| 4,759,372 | 7/1988 | Umemura et al. | 128/661.01 |
| 4,794,929 | 1/1989 | Maerfeld | 128/660.07 |
| 4,917,097 | 4/1990 | Proudian et al. | 128/661.01 |

Primary Examiner—Francis Jaworski
Assistant Examiner—George Manuel
Attorney, Agent, or Firm—Antonelli, Terry, Stout & Kraus

[57] ABSTRACT

An ultrasonic diagnostic apparatus which has a probe including a plurality of transducer elements made of an electrostrictive material arranged on a plane in two-dimensional directions, a bias applying unit for selecting the transducer elements in an arbitrary row in the horizontal direction to be in an operative condition by applying the same with a bias voltage, and a switching unit for selecting the transducer elements in at least one arbitrary column in the vertical direction by applying the same with a bias voltage, and controls the bias voltage applying unit and the switching unit to scan an ultrasonic beam in the two-dimensional directions to collect three-dimensional information on a body under inspection.

9 Claims, 12 Drawing Sheets

FIG. 1

FIG. 2A
PT 0 MOLAR %

FIG. 2B
PT 5 MOLAR %

FIG. 2C
PT 10 MOLAR %

FIG. 2D
PT 15 MOLAR %

ULTRASONIC DIAGNOSTIC APPARATUS

BACKGROUND OF THE INVENTION

This invention relates to an ultrasonic diagnostic apparatus which has a prove formed of transducer elements arranged on a plane in two-dimensional directions and scans, i.e., transmits and receives, ultrasonic beams emitted from these transducer elements in two-dimensional directions to collect three-dimensional information on a body under inspection. The invention relates more particularly to an ultrasonic diagnostic apparatus of this kind having a probe made up of an electrostrictive material which is capable of improving reliability and image quality and reducing the production cost thereof.

Figure 18:
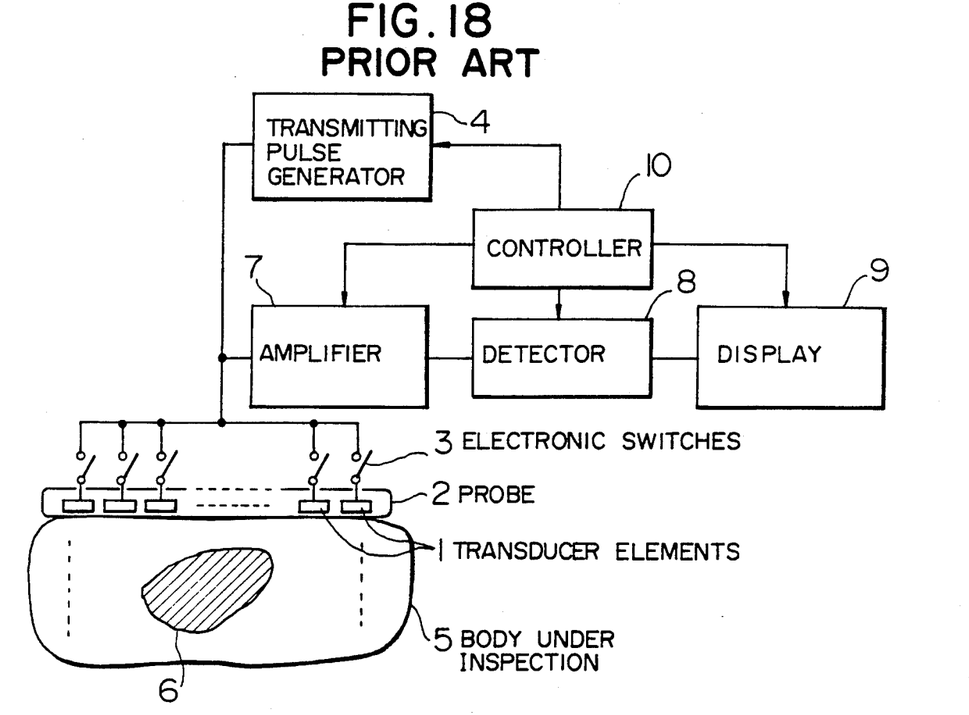
FIG. 18 is a block diagram showing a conventionally employed electronic linear scan type ultrasonic diagnostic apparatus.

An electronic linear scan type ultrasonic diagnostic apparatus conventionally used in wide application fields, as shown in FIG. 18, employs a probe 2 made up of a plurality of narrow rectangular transducer elements 1 arranged in columns. Among these transducer elements 1, a particular group is solely selected by electronic switches 3 each coupled to each of the transducer elements 1 to connect the same to a transmitting and receiving section. Each time such groups of the transducer elements thus selected are sequentially changed, a transmitting pulse generator 4 applies to each of the transducer elements 1 a high voltage pulse to emit an ultrasonic beam into a body 5 under inspection, and then a reflected echo from an objective region is received by the same group of the transducer elements 1. A signal generated by the received echo is amplified by an amplifier 7 and supplied to a detector 8 which detects a signal corresponding to the amplitude of the echo signal. An output signal from the detector 8 is supplied to a display 9 which performs a luminance modulation for positions corresponding to an ultrasonic beam emitting position and an echo reflected position of the input signal from the detector 8. Thus, a two-dimensional tomographic image of the body under inspection 5 is displayed on the display 9. A series of the above operations is performed under control of a controller 10.

Apart from the above-mentioned electronic linear scan type ultrasonic diagnostic apparatus, there are practically employed such apparatus which make it possible to observe tomographic images of a body under inspection in real time, such as an electronic curved liner scan (convex scan) type ultrasonic diagnostic apparatus, an electronic sector scan type ultrasonic diagnostic apparatus, etc, classified according to ultrasonic beam scan methods. However, either of them can provide only one arbitrary tomographic image of a body under inspection, so that it is necessary to place the probe 2 (see FIG. 18) a different locations or in different directions on the surface of the body to derive information on other sections, thereby complicating handling of the apparatus. Also, the above-mentioned conventional apparatus cannot provide information on two or more sections simultaneously in real time nor three-dimensional or solid information.

Figure 19:
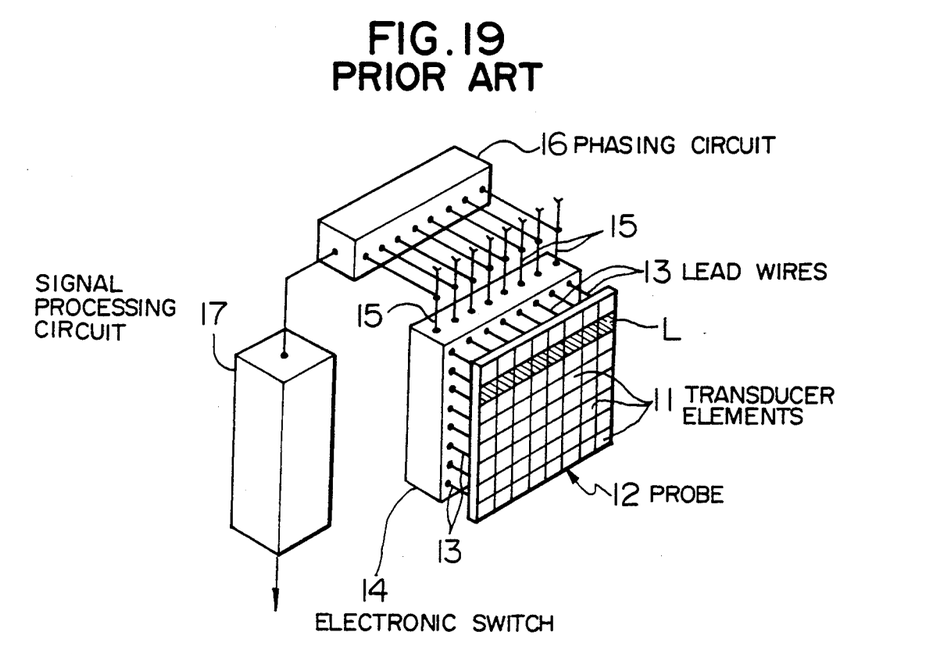
FIG. 19 is an explanatory perspective view showing the principle construction of a probe including a conventional two-dimensional array.

To attend to these problems, there is proposed to employ a probe including a so-called two-dimensional array which is formed of multiple small rectangular transducer elements arranged on a plane in two-dimensional directions, wherein a particular one or plural transducer elements are selectively operated to scan an ultrasonic beam in the two-dimensional directions, that is, to transmit and receive the ultrasonic beam in the two-dimensional directions. Such probe employing a two-dimensional array is discussed in IEEE, Trans. Sonics and Ultrasonics, SU-5 (September 1980), on Pages 273 to 280. As shown in FIG. 19, a probe 12 is made up of transducer elements 11 formed by dividing a piezo-electric material into small rectangular portions, and the transducer elements are arranged on a plane in two-dimensional directions. The transducer elements 11 arranged in a plane are each connected to lead wires 13 which in turn are connected to electronic switches 14 arranged in the two-dimensional directions from which a plurality of lead wires extend. The probe 12 of FIG. 19 is constructed such that, by selecting and closing the electronic switches 14 corresponding to the transducer elements 11 belonging to, for example, a particular row L indicated by cross-hatching in FIG. 19, the transducer elements 11 belonging to the particular row L are connected to the lead wires 15.

Figure 20:
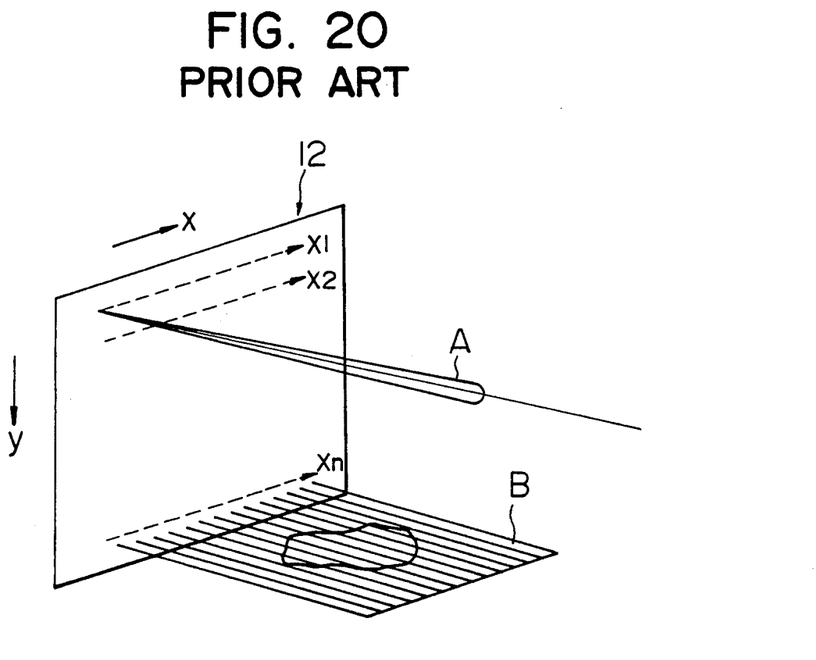
FIG. 20 is an explanatory diagram showing an electronic linear scan by the probe including the two dimensional array.
Figure 21:
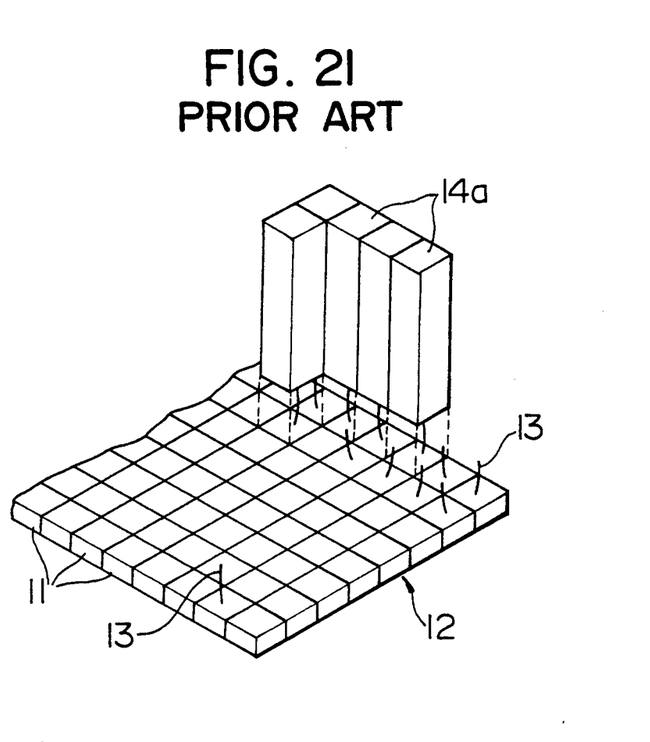
FIG. 21 is an explanatory diagram illustrating an arrangement of electronic switches and lead wires of the two-dimensional array shown in FIG. 19.

In this event, the electronic switches 14 may be closed so that a sub-group of the transducer elements group including several adjacent elements 11 solely transmit and receive an ultrasonic beam, and also signals from the transducer elements 11 may be delayed by a phasing circuit 16, so as to provide the ultrasonic beam with a converging effect. Further, the groups of the transducer elements 11 for transmitting and receiving an ultrasonic beam may be sequentially selected by latitudinally stepping the open/close control of the electronic switches 14 to perform an electronic linear scan of the ultrasonic beam. FIG. 20 shows how the electronic linear scan is performed. Specifically, in a probe including small rectangular transducer elements arranged on a plane in two-dimensional directions, an ultrasonic beam A is transferred, for example, along the first row $x_1$ in the x-direction to perform a first electronic linear scan. Next, the position of the electronic switches 19, shown in FIG. 19 is moved, for example, in the y-direction by a minute distance to transfer the ultrasonic beam A along the second row $x_2$ in the x-direction, whereby a second electronic linear scan is performed. A two-dimensional scan is achieved by thus sequentially moving such operation in the y-direction by a minute distance to transfer the ultrasonic beam A in the x-direction. Further, by piling up a plurality of ultrasonic tomographic images B in the y-direction, three-dimensional ultrasonic information on a body under inspection can be provided. A reflected echo signal derived by the above-mentioned electronic linear scan is delivered through a signal processing circuit 17 shown in FIG. 19 to a display, not shown.

Figure 22:
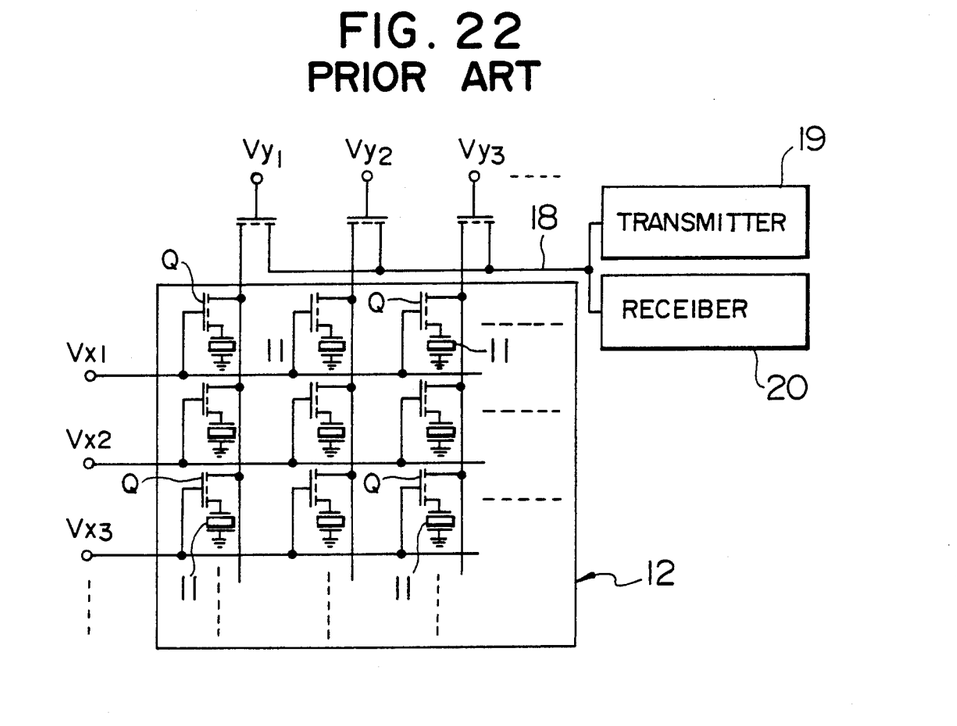
FIG. 22 is a circuit diagram showing that a group of electronic switches of the probe including the dimensional array is formed of multiple MOS FET switches.

To achieve a two-dimensional electronic linear scan by the use of the probe 12 including a two-dimensional array shown in FIG. 19, it is required to connect each of the small rectangular transducer elements arranged on a plane in the two-dimensional directions with each of lead wires 13, and also connect each of the lead wires 13 with an electronic switch 14a. Also, to dispose the multiple lead wires 13 and the electronic switches 14a on the rear side of the transducer elements 11, the electronic switches 14a each are required to have a sectional area as small as that of the transducer elements 11. There is proposed, as shown in FIG. 22 a probe in which a group of the electronic switches 14a, formed of a MOS FET integrated circuit including switches Q, is disposed on the rear side of the transducer elements 11, and signal lines 18 for selecting a particular one of the transducer elements 11 by control signals supplied to control terminals $Vx_1, Vx_2, Vx_3, \ldots$ and $Vy_1, Vy_2, Vy_3, \ldots$ are introduced from the probe to a transmitter 19 and a receiver 20. However, the probe shown in FIG. 22 has a drawback that a plurality of the transducer elements 11 cannot be operated simultaneously.

Figure 23:
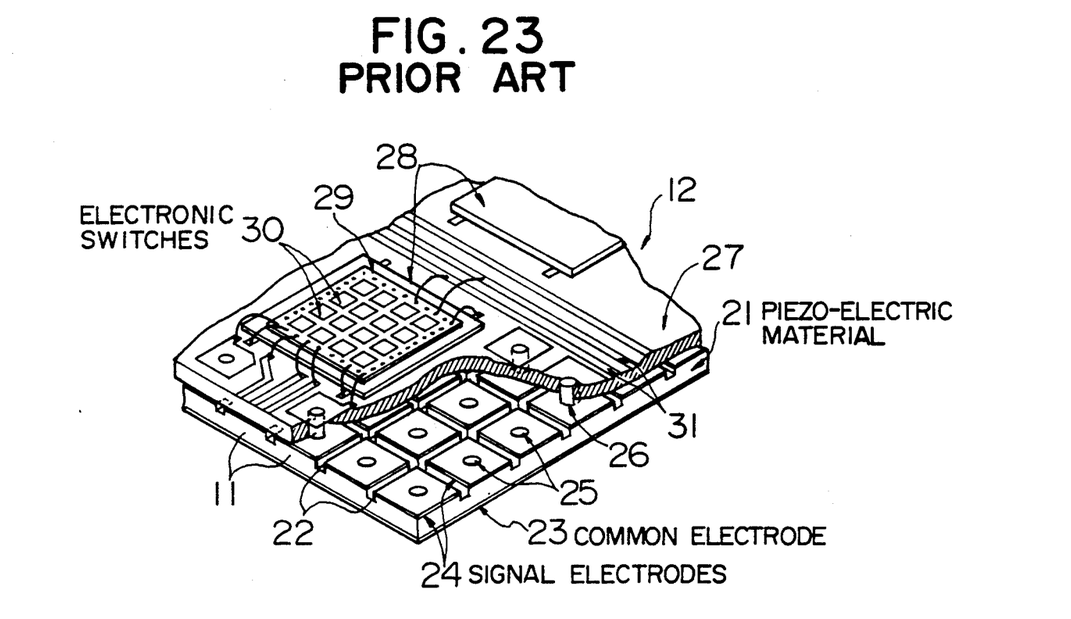
FIG. 23 is an explanatory perspective view showing a specific construction of a probe in which the circuit arrangement shown in FIG. 22 is implemented.

FIG. 23 shows a more specific construction of the conventional probe schematically shown in FIG. 22. Narrow grooves 22 are cut longitudinally and latitudinally on one side of a large single piezo-electric material 21 to divide the same into multiple small rectangular portions which constitute the transducer elements 11. These transducer elements are each provided on one and the other side thereof with a common electrode 23 and a signal electrode 24 which are opposite with one another. The common electrodes 23 are grounded while the signal electrodes 24 opposite to the common electrodes 23 each have an electrode pad 25 connected to a contact connector 26 through a sound absorbing member 27 which also serves as a support to the transducer element 11. The contact connectors 26 are each connected to a terminal of each of multiple electronic switches 30 formed on a silicon substrate 29 provided on a glass plate 28. The electronic switches 30 each have a control line and a signal output line connected to an external take-out lead 31 though which control and output signals are delivered to the outside.

The conventional probes 12 including a two-dimensional array as shown in FIGS. 19 and 23 require multiple electronic switches 14a or 30 formed of active elements for changing over transmitting and receiving signals supplied to the multiple transducer elements, in which switching noises may cause deterioration in the display quality. Also, since the sound absorbing member 27 (FIG. 23) serves as a support for the integrated circuit of the electronic switches 30 fixed thereon, a soft material or an excessively thin member cannot be employed therefor. Thus, a soft material having a good sound absorbing property cannot be freely selected, which results in insufficient performance of the sound absorbing member 27.

SUMMARY OF THE INVENTION

It is therefore an object of the present invention to provide an ultrasonic diagnostic apparatus which is capable of solving the above-mentioned problems, improving the reliability and the display quality and reducing a production cost by decreasing the number of parts used in a probe.

To achieve the above object, the present invention provides an ultrasonic diagnostic apparatus which comprises:

a probe including a plurality of transducer elements arranged on a plane in two-dimensional directions, the transducer elements being formed by dividing into small portions an electrostrictive material which induces a piezo-electric effect by a bias electric field;

electrodes provided on both sides of the transducer elements;

bias applying means for selectively applying to the transducer elements a bias voltage in order to arbitrarily select a row of the transducer elements and operate the transducer elements in the arbitrarily selected row; and switches connected with electrodes of the transducer elements for selectively operating each of the transducer elements in a direction different from the transducer element rows, wherein an ultrasonic beam scan is controlled by the bias voltage applying means and the switches. The switches are provided outside of the probe.

In the electrodes provided on both sides of the plural transducer elements, those on one side are grounded, while those on the other side belonging to each of plural columns are connected to a common signal line, and those belonging to each of plural rows are connected to a control line for applying a common bias voltage through a high impedance. This simple circuit arrangement allows the ultrasonic beam from the probe to be scanned in two-dimensional directions to collect three-dimensional information on a body under inspection.

Further, a two-dimensional arrangement of the plural transducer elements of the probe on the surface of a cylindrical body enables two planes to be scanned and thereby provides a bi-plane tomographic image.

An electrostrictive material is employed for the transducer elements, and the transducer elements themselves are provided with an electro-acoustic transducing function and a switching function for controlling the transducing function to be active or inactive, so that an integrated circuit constituting a switching circuit which is provided on the rear side of the sound absorbing member can be removed. Therefore, a sound absorbing material having a good sound absorbing property can be freely selected without limitation, which results in a significant improvement in the performance of the sound absorbing member.

BRIEF DESCRIPTION OF THE DRAWINGS

FIGS. 2A through 6 are graphs for explaining the characteristics of an electrostrictive material constituting transducer elements included in a probe of the present invention;

DESCRIPTION OF THE PREFERRED EMBODIMENTS

Embodiments of the present invention will hereinafter be explained with reference to the accompanying drawings.

Figure 1:
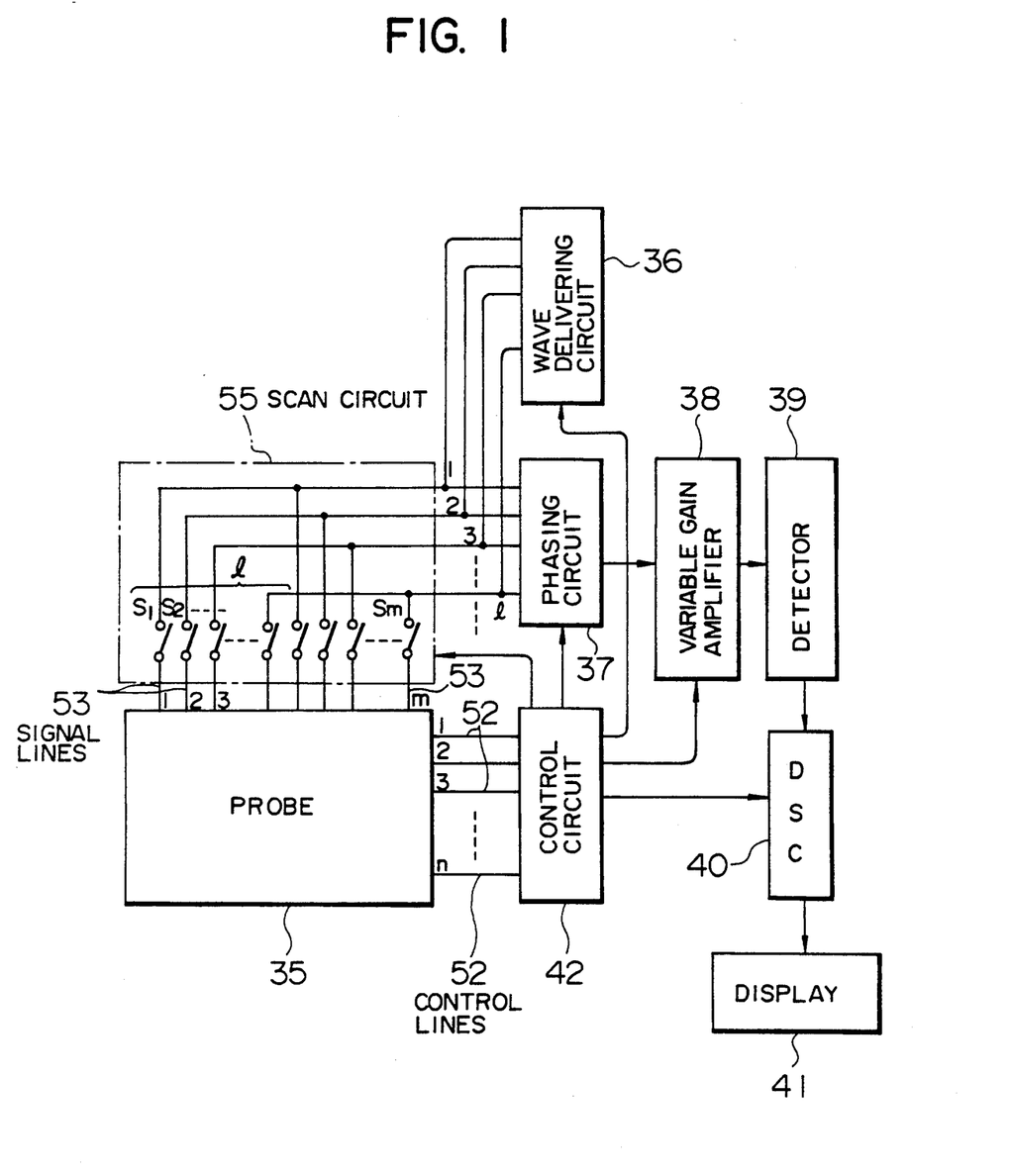
FIG. 1 is a block diagram showing an embodiment of an ultrasonic diagnostic apparatus according to the present invention.
Figure 2A:
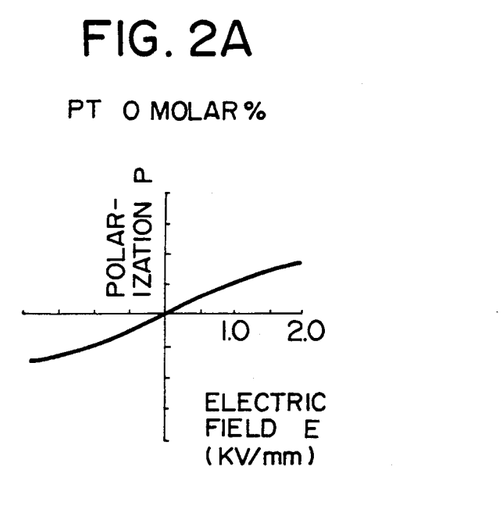
Figure 2B:
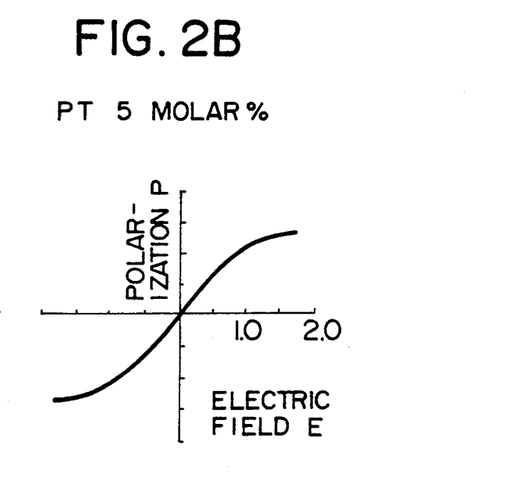
Figure 2C:
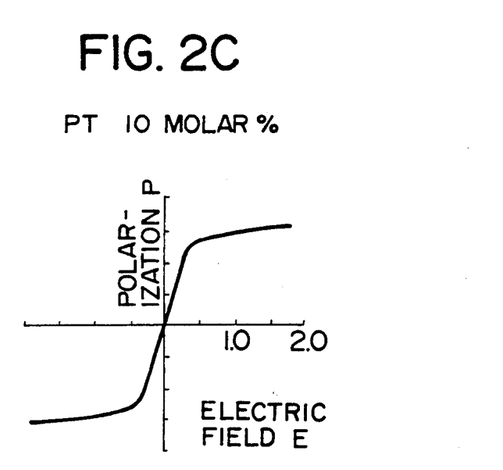
Figure 2D:
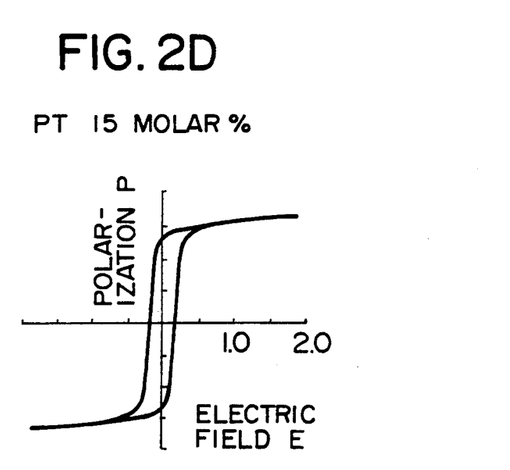

FIG. 1 is a block diagram showing an embodiment of an ultrasonic diagnostic apparatus according to the present invention. This ultrasonic diagnostic apparatus is adapted to collect three-dimensional dimensional information on a body under inspection by scanning an ultrasonic beam emitted from transducer elements arranged in two-dimensional directions, and includes a probe 35, a wave delivering circuit 36, a phasing circuit 37, variable gain amplifier 38, a detector 39, a digital scan converter (hereinafter called "DSC" for short) 40, a display 41 and a control circuit 42.

The probe 35, which is adapted to scan an ultrasonic beam in two-dimensional directions, includes transducer elements arranged on a plane in a matrix of rows and columns for transmitting and receiving the ultrasonic beam. The wave delivering circuit 36, for delivering a wave delivering pulse to the probe 35, has, for example, l pulse generators, and is adapted to converge the ultrasonic beam at a location a predetermined distance from the probe 35 by providing each channel with an arbitrary delay time. The phasing circuit 37 is adapted to receive reflected echo signals (echo signals) of, for example, l channels received by the probe 35 and to give a predetermined delay time to the echo signals to provide a sharp directing characteristic to a signal at a particular location. The delay times given to the wave delivering circuit 36 and the respective channels of the phasing circuit 37 can be controlled by a control circuit 42, later referred to. The variable gain amplifier 38 is adapted to receive an output signal from the phasing circuit 37 and compensate for the received signal which becomes weaker as a reflected echo is generated at a deeper part of a body under inspection. The detector 39 is adapted to receive an output signal from the variable gain amplifier 38 and to detect the amplitude of an echo signal. The DSC 40 is adapted to receive an output signal from the detector 39, convert the output signal from an analog form to a digital form, write the digitally converted signal into a video memory, convert video data read out of the video memory to a standard television signal and output the standard television signal. The display 41 is adapted to receive an output signal from the DSC 40 and display a tomographic image formed by reflected echoes of the ultrasonic beams emitted to a body under inspection. The control circuit 41 is adapted to control a series of operations performed by the wave delivering circuit 36, the phasing circuit 37, the variable gain amplifier 38 and the DSC 40.

The probe 35 of the present invention has transducer elements formed by dividing into small portions a electrostrictive material which induces a piezo-electric effect by a bias electric field. These plural transducer elements are arranged in a two-dimensional array in a plane, and each of them are provided with electrodes on both sides of the transducer element. Also, the probe 35 is provided with means for selectively applying the transducer elements with a bias voltage in order to operate the transducer elements in rows and switches connected with the electrodes of the transducer elements for selectively operating each of the transducer elements in a direction different from the above moving direction in rows, whereby the ultrasonic beam scan is controlled.

Next, an electrostrictive material constituting the transducer elements of the probe will be explained. The electrostrictive material induces a piezo-electric effect by a bias electric field, by which its electro-acoustic transducing efficiency can be controlled, and made of, for example, a PMN-PT ferroelectric relaxor ceramics, where PMN represents a substance expressed by the following chemical formula:

$Pb(Mg_{1/3}Nb_{2/3})O_3$ and PT represents a substance (lead titanate) expressed by the following chemical formula:

$PbTiO_3$

Such electrostrictive material constituted of the PMN-PT ceramics is described in detail in "Material for Ultrasonic Probe" for the seventh meeting of Applied Ferroelectric Materials and Applications (from May 31 to June 2, 1989), and has characteristics as explained below.

In the PMN-PT ceramics, electric field to polarization hysteresis curves measured with samples including 0 to 15 molar percent of $PbTiO_3$ (lead titanate, hereinafter written "PT" for short) at a room temperature are as shown in FIGS. 2A to 2D. It can be seen from the experimental results that the hysteresis is small in the vicinity of ten molar percent of PT, wherein a relatively low electric field E can induce polarization P in a similar level to a strong electricity inducing phase. Considering the utility of the case where the electrostrictive material including this PMN-PT ceramics is applied to a probe for an ultrasonic diagnostic apparatus, the electromechanical coupling coefficient Kt may be evaluated which is induced by a bias electric field intensity below 400 V/mm with respect to an applicable voltage. Specifically, a larger coefficient Kt shows a higher sensitivity.

Figure 3A:
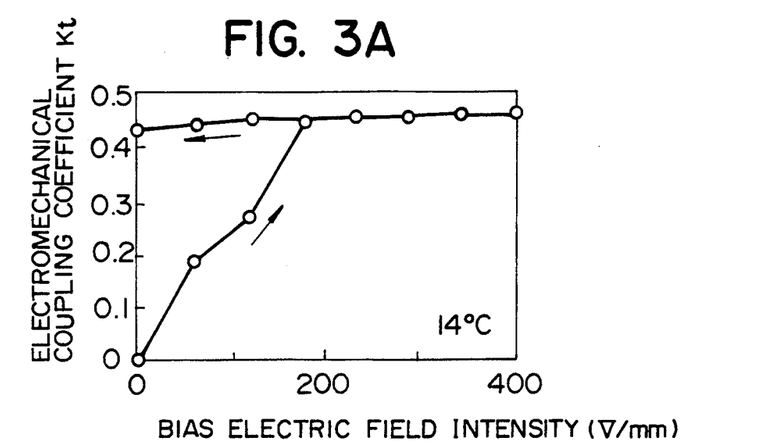
Figure 3B:
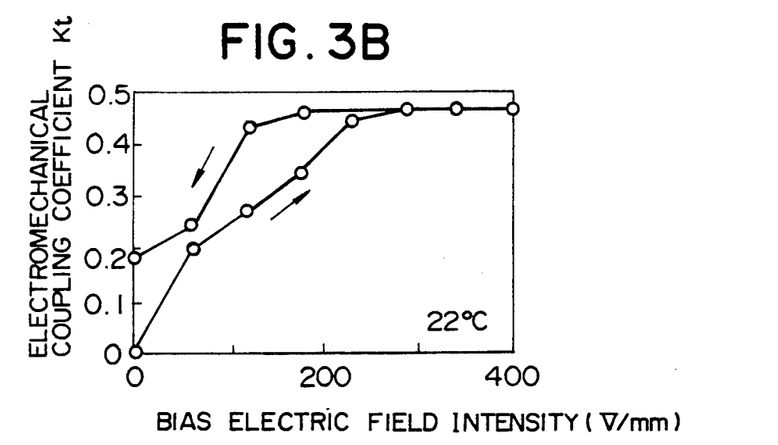
Figure 3C:
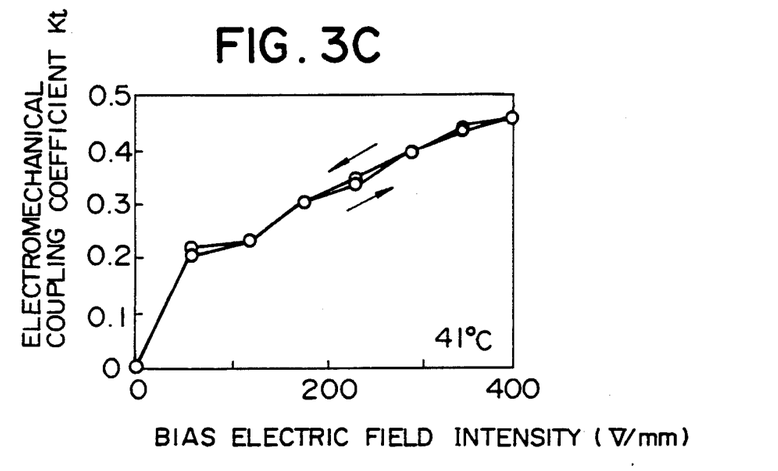

FIGS. 3A to 3C show variations of the electromechanical coupling coefficient Kt when a material including ten molar percent of PT, after maintained at 70° C., is applied with an increasing and decreasing direct current bias voltage at temperatures of 14° C., 22° C. and 41° C., respectively. FIG. 3A shows that the coefficient Kt remains by applying the bias voltage, which is therefore called "a strong dielectric phase". FIG. 3C shows that the coefficient Kt does not remain even by applying the bias voltage, so that this is called "a normal dielectric phase". Further, FIG. 3B shows an intermediate condition between the phases shown in FIGS. 3A and 3C. Thus, an electrostrictive material employing a mild ferroelectric substance having a phase transition temperature in the vicinity of room temperature has the electromechanical coupling coefficient Kt largely varied by temperature, however, it is desirable for practical use that the coefficient Kt is not varied by temperature. When an optimal composition of a material for a probe is examined in consideration of the above-mentioned property, it is desired that no electromechanical coupling coefficient Kt remains in a range of usable environmental temperature, as shown in FIG. 3C. It can be said from FIG. 3C that a material including ten molar percent of PT may be applied to practical use if a probe made of such material is always used at a temperature of approximately 40° C.

Figure 4:
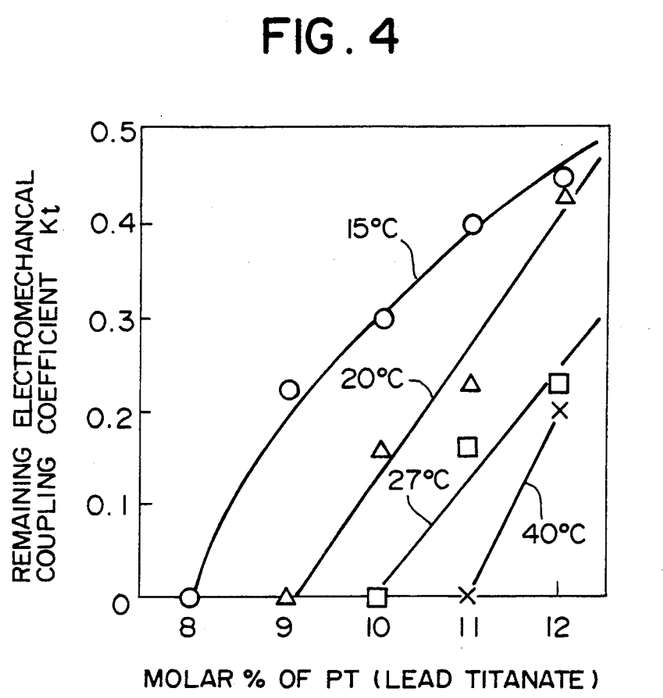
Figure 5:
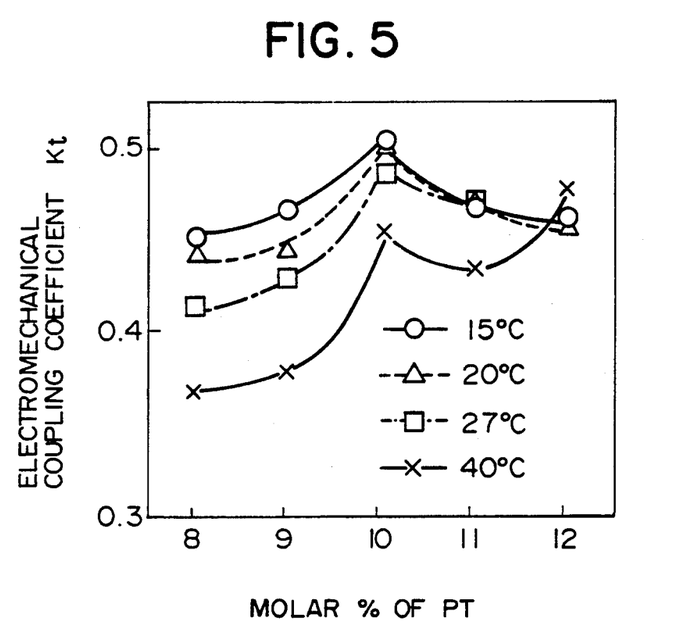

Next, FIG. 4 shows the relationship between the electromechanical coupling coefficient Kt remaining in the above electrostrictive material after being subjected to a bias electric field intensity of 400 V/mm and the molar concentration of PT in the electrostrictive material, with the temperature being a parameter. As can be understood from FIG. 4, an electrostrictive material including PT at a molar concentration below nine molar percent can realize no remaining Kt in a temperature range between 20° C. and 40° C. Further, FIG. 5 shows the relationship between the electromechanical coupling coefficient Kt induced by applying the electrostrictive material with a bias electric field intensity of 400 V/mm and the molar concentration of PT in the electrostrictive material, with the temperature being a parameter. It is understood from FIGS. 4 and 5 that it is an electrostrictive material including nine molar percent that presents no remaining coefficient Kt and the largest coefficient Kt when it is subjected to a bias voltage in a temperature range between 20° C. and 40° C. When such material is subjected to a bias electric field intensity of 400 V/mm at a temperature of 20° C., the coefficient Kt is approximately 0.5, which is the same characteristic as that obtained by PZT as a piezo-electric material employed in current ultrasonic diagnostic apparatus, so that it is assumed that a similar sensitivity to that presented by PZT is obtained by the electrostrictive material including nine molar percent of PT. From the above discussion, it is understood that an electrostrictive material constituted of properly composed PMN-PT ceramics can realize a probe which is capable of controlling the electro-acoustic transducing efficiency by a bias electric field without employing active elements.

Figure 6:
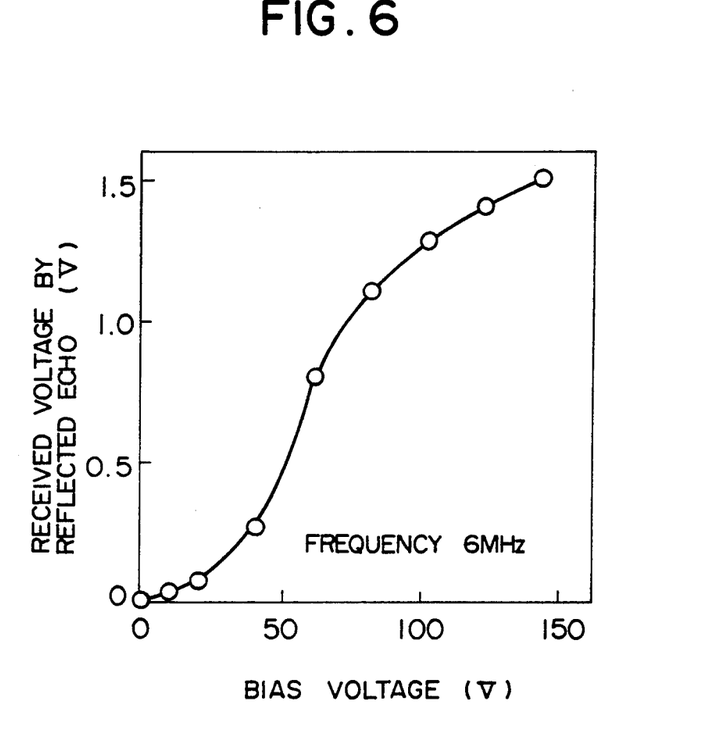
Figure 7:
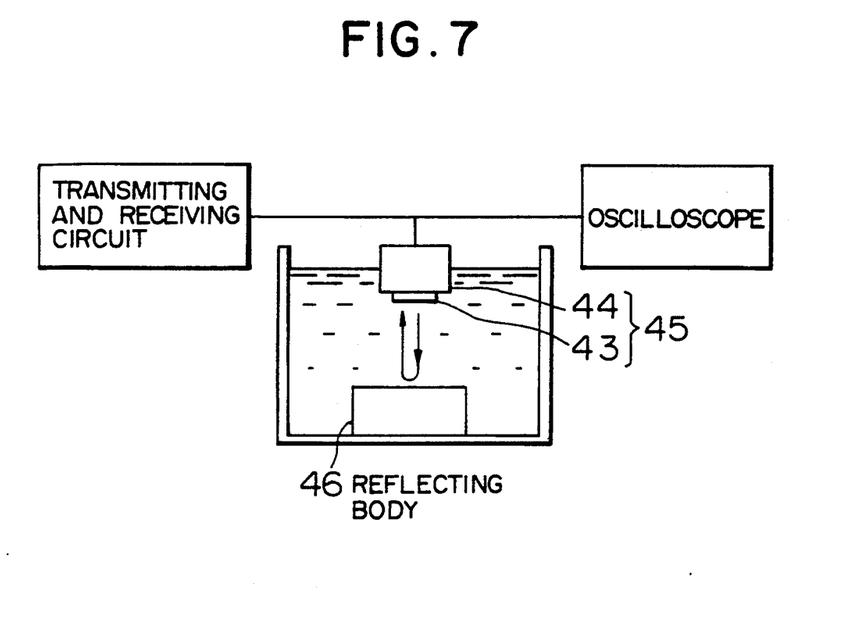
FIG. 7 is an explanatory diagram showing an apparatus for experimenting with the characteristics of a probe made of the electrostrictive material.

FIG. 6 is a graph showing an experimental result with respect to a probe made of an electro-strictive material constituted of the above-mentioned PMN-PT ceramics. This experiment employs a probe 45 including, for example, a disk-shaped transducer 43 attached to the front surface of a rear braking member 44. As shown in FIG. 7, the probe 45, which is being subjected to a direct current bias voltage, is driven to emit an ultrasonic beam to substantially perfect reflecting body 46 made of flat metal plates placed under water. A reflected echo from the reflecting body 46 is received by the probe 45, thus making an experiment of transmitting and receiving an ultrasonic beam according to a pulse echo method. The relationship between the bias voltage applied to the probe 45 and a voltage generated from a reflected echo received by the probe 45 is as shown in FIG. 6. Specifically, when the bias voltage is zero, the received voltage is also zero. As the bias voltage is increased, the received voltage is also increased. It is thus understood that the electro-acoustical conversion efficiency can be controlled by a bias voltage.

Figure 8:
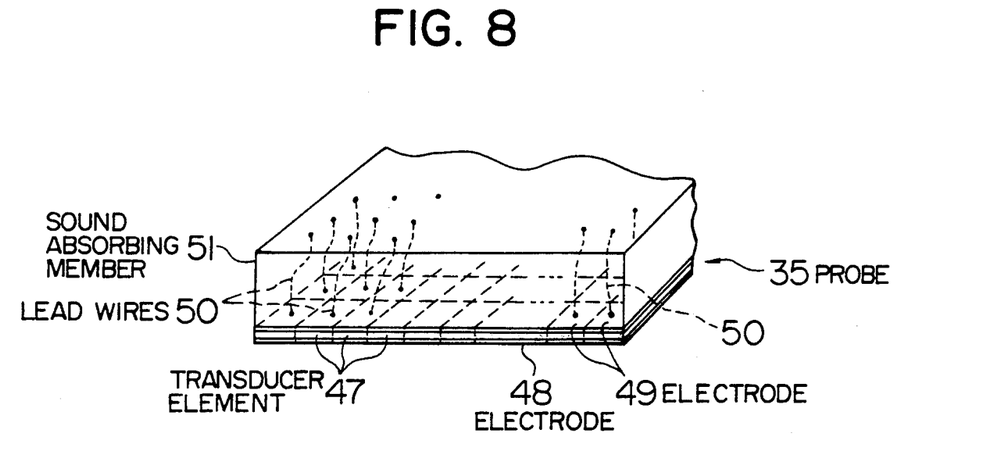
FIG. 8 is a perspective view showing the construction of a probe of the present invention.

Based on the above discussion, the present invention employs, as a material constituting the transducer elements of the probe 35 shown in FIG. 1, an electrostrictive material in which a piezo-electric effect is induced by a bias voltage and the electroacoustical conversion efficiency is controlled also by the bias voltage. This electrostrictive material is divided into multiple rectangular portions, each of which forms a transducer element 47. These multiple transducer elements 47 are arranged in a two-dimensional array in a plane and each is provided with electrodes 48, 49 on the respective sides thereof, thus constructing the probe 45. The electrodes 4 disposed on the front side of the transducer elements 47 are commonly connected to the ground, while the other electrodes 49 disposed on the rear side are each connected to the lead wires 50 which are taken out backward through the sound absorbing member 51 disposed on the rear side.

Figure 9:
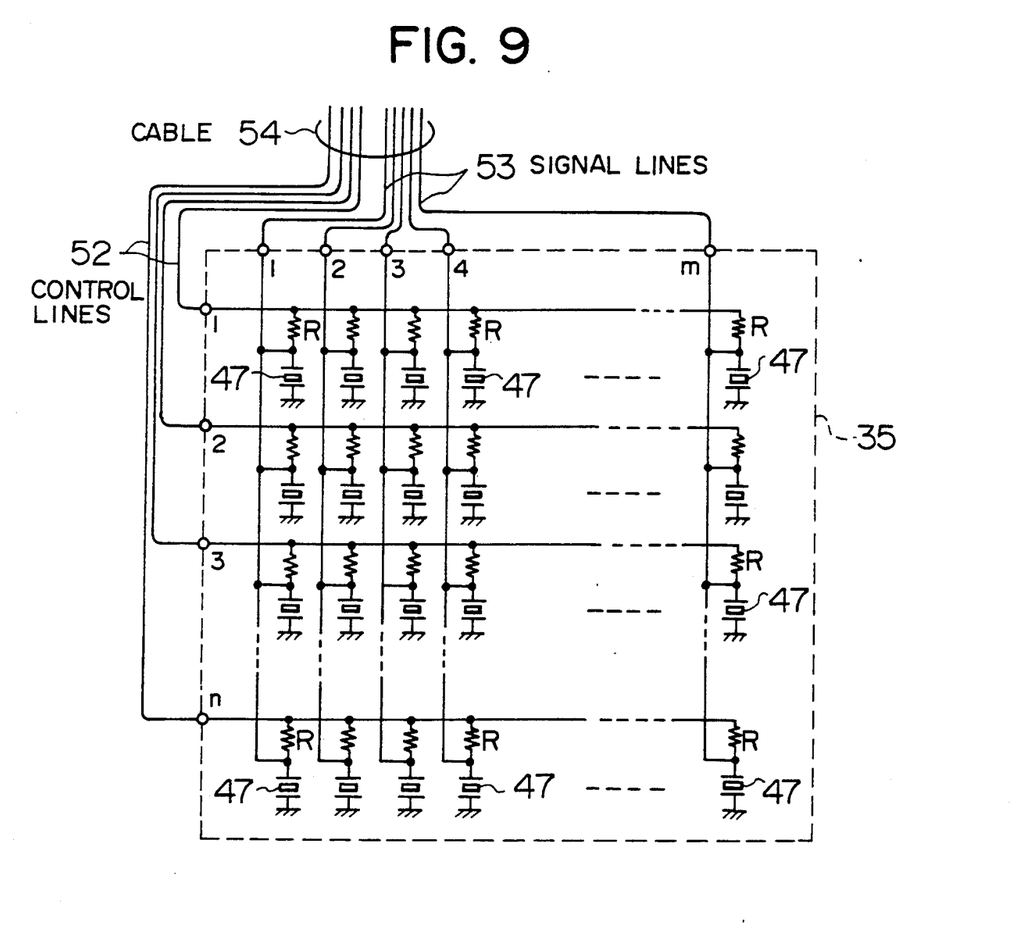
FIG. 9 is a circuit diagram showing a circuit arrangement of the probe shown in FIG. 8.

The multiple transducer elements 47 constituting the probe thus constructed has a circuit arrangement as shown in FIG. 9. Specifically, the multiple transducer elements 47 are arranged, for example, in a matrix of m (in the vertical direction) x n (in the horizontal direction). The transducer elements 47 aligned in rows in the horizontal direction are commonly connected to respective control lines 52 through sufficiently large resistors R, while the respective transducer elements 47 aligned in columns in the vertical direction are commonly connected to respective signal lines 53. There are provided n of the control lines 52. It is possible to increase the electromechanical coupling coefficient Kt of the transducer elements 47 aligned in a particular row in the horizontal direction by applying a bias voltage to the control line 52 connected to the particular line. It is also possible to decrease the electromechanical coupling coefficient Kt of the transducer elements aligned in a particular row to zero by removing the bias voltage. Therefore, the transducer elements 47 aligned in a particular row in the horizontal direction can be controlled to be active or inactive as electro-acoustic transducing elements by turning on and off the bias voltage applied to the control lines 52. In other words, it is possible to effect the same operation as the example shown in FIG. 19 in which the transducer elements 11 belonging to a particular line L are allowed to transmit and receive an ultrasonic beam. The resistor R having a high resistance value is an element for providing a higher impedance than the load of the transducer elements so as to protect transmitting and receiving signals from flowing through the control lines 52 to the transducer elements 47 arranged in the horizontal direction.

Also, there are m signal lines 53 through which a transmitting signal voltage is supplied to and a received signal voltage is delivered from the transducer elements 47 aligned in the columns in the vertical direction. This arrangement allows the transducer elements to sequentially scan the ultrasonic beam from one end to the other end in a particular row activated by the bias voltage from the control line 52. Thus, the probe 35 of the present invention shown in FIGS. 8 and 9 can perform the same operations as the conventional probe shown in FIG. 19. Incidentally, in FIG. 9, the control lines 52 and the signal lines 53 are collected in a single cable 54 which is taken out of the probe 35.

The control lines 52, as means for applying a bias voltage for operating the transducer elements 47 of the probe 35 in rows, are controlled by the control circuit 42 shown in FIG. 1. On the other hand, the signal lines 53 are connected to a scan circuit 55 which serves as means for selecting the respective transducing elements 4 in a direction different from the moving direction in rows and controlling the scanning of the ultrasonic beam. The scan circuit 55 includes, for example, m electronic switches $S_1, S_2, \ldots, S_m$ which are connected to m of the signal lines 53, respectively. Then, by closing, for example, l adjacent ones of the electronic switches $S_1$ to $S_m$, l transducer elements 47 in the direction different from the row direction are selected as a group. Further, by sequentially changing over l electronic switches one by one, the transducer elements 47 in the selected group can be changed over one by one. It is therefore possible to perform a stepping scan of the ultrasonic beam in a particular row of the transducer elements.

A series of the above-mentioned operations performed by the scan circuit 55 are controlled by the control circuit 42. By the above-mentioned operations, it is possible to perform a two-dimensional scan by sequentially moving the electronic linear scan in the x-direction by a minute distance along the y-direction.

Figure 10A:
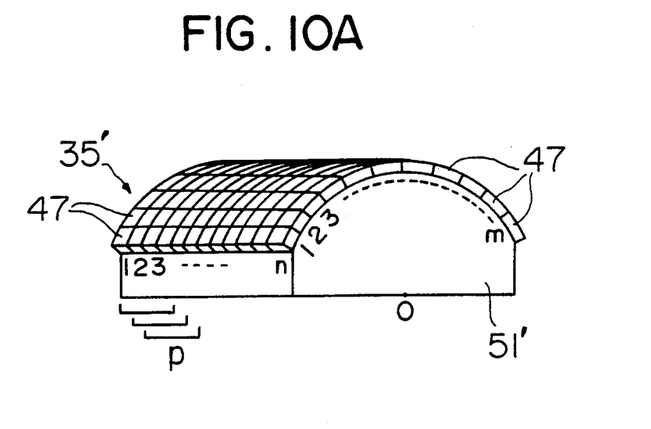
FIG. 10A and FIG. 10B are a perspective view and a lateral view showing a modified example of the probe of the present invention.
Figure 10B:
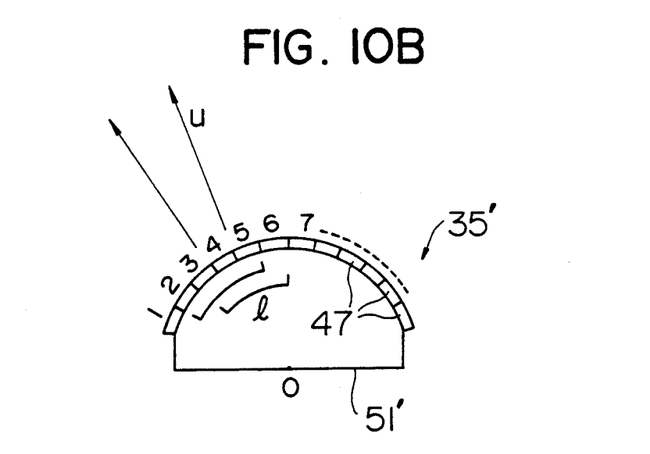

FIGS. 10A and 10B are respectively a perspective view and a lateral view for explaining an modified example 35' of the probe 35 according to the present invention. The modified probe 35' has a sound absorbing member 51' formed as a half cylindrical body, as shown in FIG. 10A, and multiple transducer elements 47 are arranged on a convex plane in the circular arc direction of the curved plane and in the direction of the central shaft 0 of the cylindrical body (longitudinal direction). In this arrangement, the transducer elements 47 are aligned in the first to (n)th rows along the longitudinal direction as a sound absorbing member 51' formed of the half cylindrical body. In this alignment, a bias voltage is applied through the control lines 52 only to p adjacent transducer elements 47 in the n rows of the transducer elements 47 to select the same for operation. In this event, the position in a group of the p transducer elements 47 can be sequentially moved one by one under control of the control lines 52 which applies the bias voltage to the transducer elements 47, whereby a scan in the row direction can be performed. Meanwhile, a scan in the column direction is performed by controlling the m electronic switches $S_1$—$S_m$ shown in FIG. 1, as described above, where the ultrasonic beam is scanned in and reaction indicated by an arrow u, as shown in FIG. 10B, in the same manner as a conventional sector scan performed by a so-called convex type probe.

Figure 11:
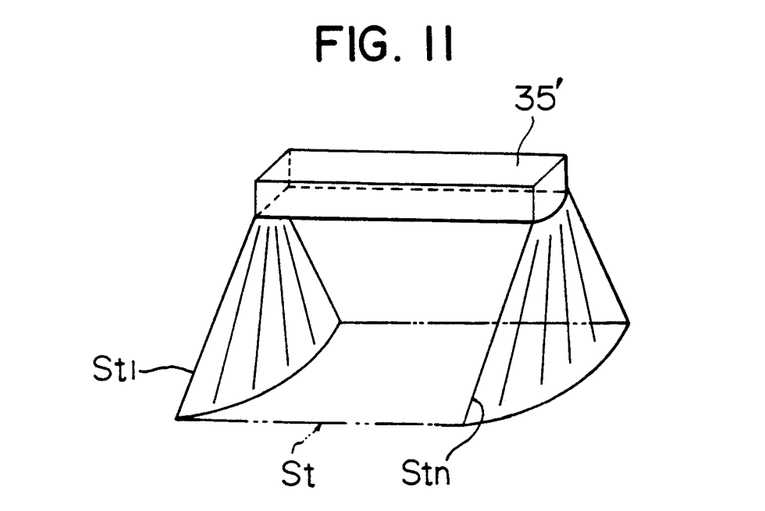
FIGS. 11 and 12 are explanatory diagrams showing a scanning condition of an ultrasonic beam by the exemplary probe shown in FIG. 10.

The ultrasonic beam emitted into a body under inspection by the above-mentioned scan in the two directions is such as shown in FIG. 11. A scan plane $St_1$ indicates a first scan plane formed by a sector scan performed by the transducer elements 47 belonging to a circular arc direction which are selected by applying the bias voltage to the transducer elements 47 in the first to (p)th rows. Also, another scan plane Stn indicates a (n)th scan plane formed by a sector scan performed by the transducer elements 47 in the last p rows including the (n)th row which are selected by applying the same with the bias voltage. Between the first scan plane $St_1$ and the (n)th scan plane Stn there are formed multiple sector type scan planes by which a solid scan region St is formed and thereby three-dimensional information on a body under inspection can be collected.

Figures 12, 13, 14:
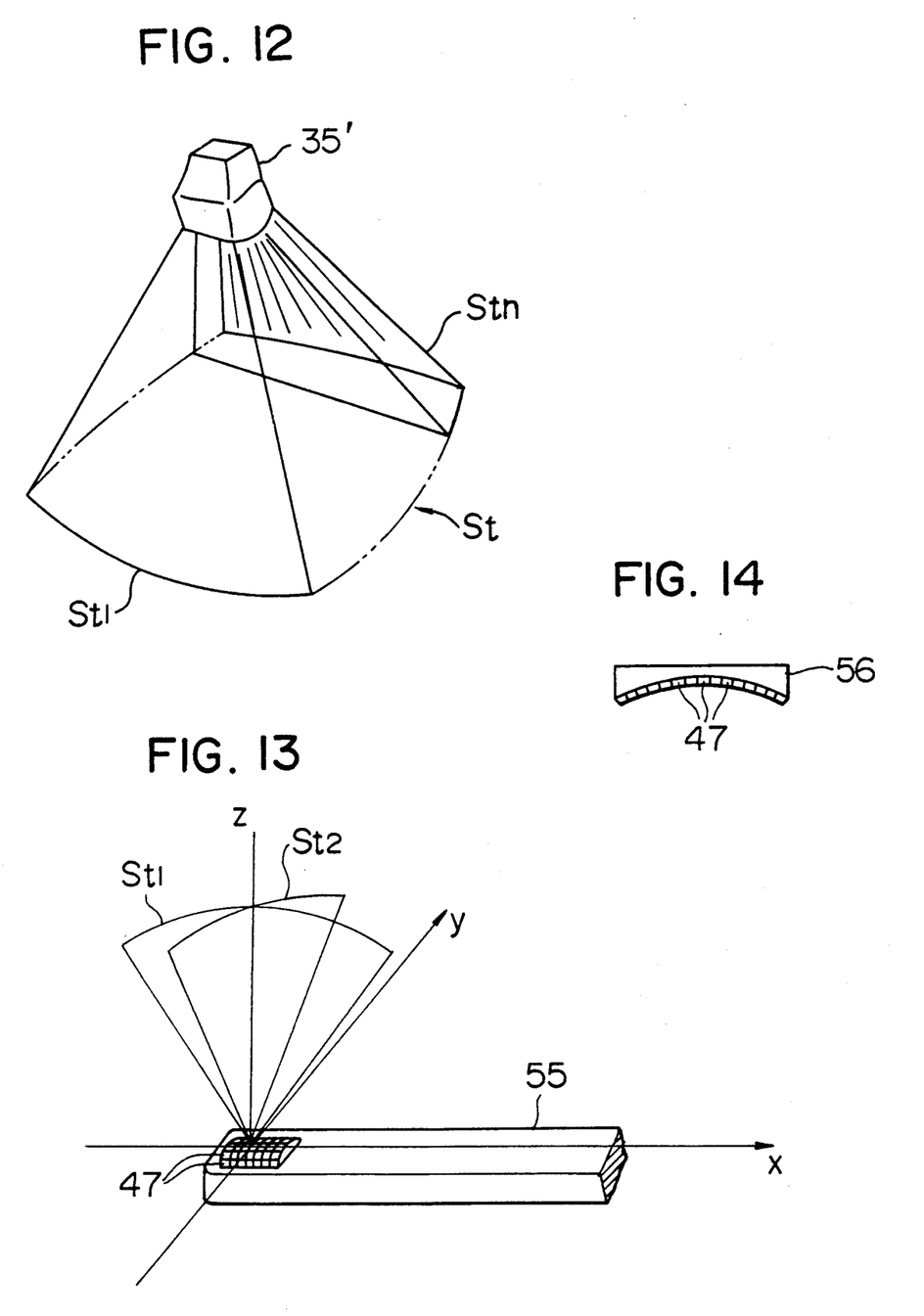
FIG. 13 is an explanatory diagram illustrating an example of applying the probe shown in FIG. 10 to an intra-luminal probe.
FIG. 14 is an explanatory diagram showing that an acoustic lens is attached to an external plane of the transducer elements shown in FIG. 13.

FIG. 12 is an explanatory diagram showing another scan region formed by the operation of the probe 35', the construction of which is shown in FIG. 10. In this event, the signals generated by the transducer elements 47 aligned in the direction of the central axis of the sound absorbing member 51 formed of a half cylindrical body shown in FIG. 10A are all employed and arranged in phase to control the direction of the ultrasonic beam, that is, a sector scan by a so-called phased array is performed. Meanwhile, the transducer elements 47 aligned in the circular arc direction of the curved surface of the sound absorbing member 51' are controlled to perform a linear scan by controlling the bias voltage. FIG. 12 shows a scan region formed by the above-mentioned two-dimensional scan. In this example, information on a three-dimensional space defined by the first sector type scan plane $St_1$ and the (n)th scan plane Stn can be collected.

FIG. 13 is an explanatory diagram showing an example of applying the probe 35' shown in FIGS. 10A and 10B to an intraluminal probe 55. In this application example, the central axis O of the sound absorbing member 51' shown in FIG. 10A is directed to the longitudinal direction of the intraluminal probe 55, and the circular arc direction of the curved surface is directed to the direction of the convex surface of the intraluminal probe 55, thereby forming the probe 55. Such arrangement makes it possible to form a first sector type scan plane $St_1$ by the phased array and a second sector type scan plane $St_2$ by the same operation as a convex type probe. Thus, the probe 55 can provide scan planes in two orthogonal planes, that is, the first scan plane $St_1$ on the x-z plane and the second scan plane $St_2$ on the y-z plane. Therefore, by alternating formation of tomographic images on the scan planes $St_1$ and $St_2$ at a high speed, a bi-plane tomographic image can be produced which allows the operator to observe tomographic images in orthogonal directions at the same position in real time. In this event, if two scan planes which are not orthogonal to one another are selected, two tomographic images in two different directions with one another may be produced.

In the above application example, the ultrasonic beam emitted from the transducer elements 47 is allowed to perform a converging action if the probe 55 is provided with an acoustic lens 56 which is mounted on a plane outside a section of the y-z plane of the transducer elements as shown in FIG. 14. The acoustic lens 56 may be made of a material in which the acoustic velocity is higher than in a body under inspection. Also, the acoustic lens 56 is formed such that the radius of curvature of the outer surface is larger than that of the inner surface. The provision of such converging action can improve the bearing discrimination of the ultrasonic beam.

Figure 15:
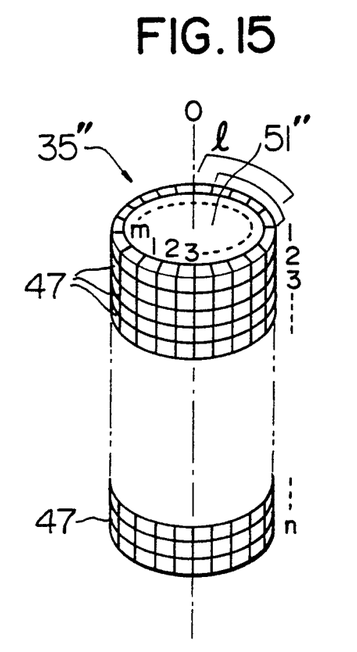
FIG. 15 is an explanatory perspective view showing another modified example of a probe according to the present invention.
Figure 16:
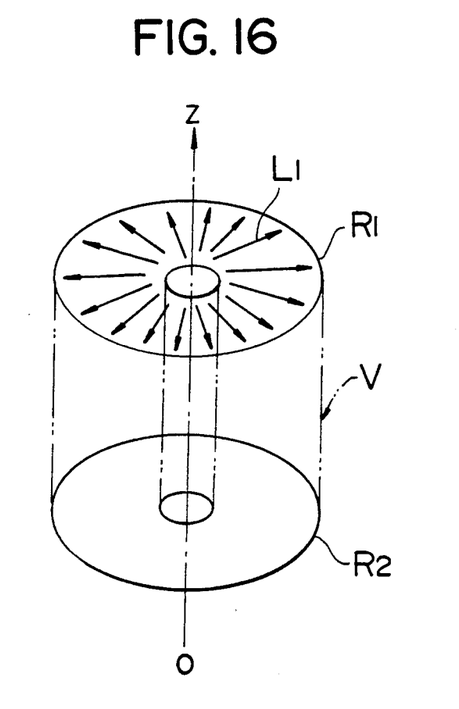
FIG. 16 is an explanatory diagram showing a scanning condition of an ultrasonic beam by the exemplary probe shown in FIG. 15.

FIG. 15 is a explanatory perspective view showing a further modified example (35") of the probe 35 according to the present invention. The probe 35" of this modified example has a sound absorbing member 51" formed of a cylindrical body on which the multiple transducer elements 47 are aligned in the circumferential direction of the curved surface of the sound absorbing member 51" and the direction of the central axis O of the cylindrical body. In this arrangement, the transducer elements 47 are disposed in the first row to the (n)th row along the longitudinal direction of the cylindrical sound absorbing member 51" and in the first column to the (m)th column along the circumferential direction. Each group of the transducer elements 47 aligned in the rows are connected to the control line 52, and each group in the columns are connected to the signal line 53, in the same manner as the arrangement shown in FIG. 9. To perform a radial scan along the circumference by thus connected signal lines 53, a group of, for example 1 adjacent transducer elements 47 are first selected under control of the electronic switches $S_1$—$S_m$ shown in FIG. 1, such group of the transducer elements 47 for transmitting and receiving the ultrasonic beam is sequentially moved along the circumferential direction. Incidentally, the position with respect to the central axis O of the cylindrical sound absorbing member 51 for the radial scan is controlled to be sequentially moved by the bias voltage applied from the control lines 52 to the transducer elements 47 in the row direction. Therefore, a radial scan plane formed by the above operation is obtained by performing a linear scan from a top end radial scan plane $R_1$ to a bottom end radial scan plane $R_2$ along the central axis O of the generally cylindrical probe 35". In this example, a diagnostic region in a body under inspection is defined by a cylindrical space V between the radial scan planes $R_1$ and $R_2$. In this condition, if a scan line in a particular direction, for example, a scan line $L_1$ in the top end radial scan plane $R_1$ is linearly scanned along the Z axis, a linear scan plane in the particular direction can be formed. Thus, an arbitrary radial scan plane or linear scan plane in the space V, shown in FIG. 16, can be formed by the above-mentioned operations.

Figure 17:
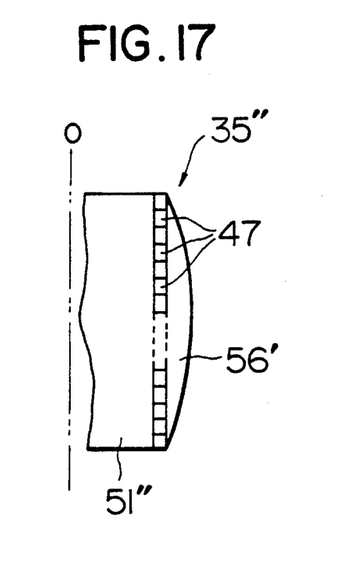
FIG. 17 is an explanatory diagram showing that an acoustic lens is attached to an external plane of the transducer elements shown in FIG. 15.

In the above modified example, if an acoustic lens 56', made of a material in which the acoustic velocity is lower than in a body under inspection, for example, silicon rubber and having a convex section, is attached to an outer peripheral surface of a section including the central axis O of the probe 35", the ultrasonic beam emitted from the transducer elements 47 is allowed to perform a converging action. The provision of such converting action can improve the bearing discrimination of the ultrasonic beam in a linearly scanning direction. The modified probe 35" shown in FIG. 15 is particularly effective in realizing an intraluminal scan for a region including the rectum.

We claim:

1. An ultrasonic diagnostic apparatus comprising:
   (a) a probe including a plurality of transducer elements made of an electrostrictive material arranged in two-dimensional directions so as to form an $n \times m$ matrix of rows and columns;
   (b) bias applying means for selecting transducer elements in an arbitrary row by applying a bias voltage thereto so that said selected transducer elements are rendered in an operative condition;
   (c) switching means for selecting transducer elements in at least one arbitrary column by applying a bias voltage thereto;
   (d) means for controlling said bias voltage applying means and said switching means to scan an ultrasonic beam in the two-dimensional directions of said $n \times m$ matrix; and
   (e) means for collecting three-dimensional information on a body under inspection based on echo signals received in response to said two-dimensional scan.

2. An ultrasonic diagnostic apparatus according to claim 1, wherein each of said transducer elements is provided with a respective electrode on opposite surfaces thereof, said electrode on a first surface being grounded, said electrode on a second surface being connected to a high impedance and said bias voltage applying means.

3. An ultrasonic diagnostic apparatus according to claim 2, wherein said electrodes on said first surface of said transducer elements aligned in each row are connected through said high impedance to a common control line extending from said bias voltage applying means, and said electrodes on said second surface of said transducer elements aligned in each column are connected to a common signal line extending from said bias voltage applying means.

4. An ultrasonic diagnostic apparatus according to claim 1, wherein said matrix of transducer elements is disposed on a cylindrical surface with the rows aligned in the circumferential direction of the surface and the columns aligned in the axial direction thereof.

5. An ultrasonic diagnostic apparatus according to claim 4, wherein said switching means has means for forming scan planes in two different directions, and said means for collecting three-dimensional information includes means for collecting information on bi-plane tomographic images.

6. An ultrasonic diagnostic apparatus according to claim 1, wherein said probe is formed of said plural transducer elements aligned in two-dimensional directions and disposed at least on a partial cylindrical surface.

7. An ultrasonic diagnostic apparatus according to claim 1, wherein said probe is an intraluminal probe.

8. An ultrasonic diagnostic apparatus according to claim 1, wherein said probe has an acoustic lens made of a material in which acoustic velocity is higher than said body under inspection.

9. An ultrasonic diagnostic apparatus according to claim 1, wherein said probe has an acoustic lens made of a material in which acoustic velocity is lower than said body under inspection.

* * * * *